United States Patent [19]

Weinberg et al.

[11] Patent Number: 4,616,655

[45] Date of Patent: Oct. 14, 1986

[54] IMPLANTABLE PULSE GENERATOR HAVING A SINGLE PRINTED CIRCUIT BOARD AND A CHIP CARRIER

[75] Inventors: Alvin H. Weinberg, Miami; W. Kinzy Jones, Pembroke Pines, both of Fla.

[73] Assignee: Cordis Corporation, Miami, Fla.

[21] Appl. No.: 572,310

[22] Filed: Jan. 20, 1984

[51] Int. Cl.⁴ .............................................. A61N 1/00
[52] U.S. Cl. .................................. 128/419 P; 357/80; 361/401
[58] Field of Search ....... 128/419 P, 419 PG, 419 PS; 339/17 B, 17 CF, 17 E, 17 LM, 17 M, 17 N; 361/394–395, 415; 357/72, 74, 80; 29/588, 831–832, 841; 174/52 FD, 52 PE

[56] References Cited

U.S. PATENT DOCUMENTS 4,288,841  9/1981  Gogal ................................... 361/401
4,399,819  8/1983  Cowdery ......................... 128/419 P
4,445,274  5/1984  Suzuki et al. ......................... 357/80

Primary Examiner—William E. Kamm
Attorney, Agent, or Firm—Yount & Tarolli

[57] ABSTRACT

The implantable pulse generator herein may take the form of a cardiac pacer. The generator includes a pulse generator circuit including passive and active chips. These are mounted on a chip carrier with the active chips located in a hermetically sealed cavity in one major surface of the carrier and the passive chips are mounted on the other major surface. Conductive means internally of the carrier provide electrical paths interconnecting the active and passive chips.

9 Claims, 9 Drawing Figures

FIRST CONDUCTOR LEVEL     ⊕ – VIA TO SECOND CONDUCTOR LEVEL (I.E. LAYER 42)

SECOND CONDUCTOR LEVEL

⊕ - LAND AREA FOR VIA FROM FIRST CONDUCTOR LEVEL (I.E. LAYER 44)

⊘ - VIA TO THIRD CONDUCTOR LEVEL (I.E. BOTTOM OF LAYER 40)

THIRD CONDUCTOR LEVEL

⊘ - LAND AREA FOR VIA FROM SECOND CONDUCTOR LEVEL (I.E. LAYER 42)

⊕ - VIA TO FOURTH CONDUCTOR LEVEL (I.E. TOP OF LAYER 40)

IMPLANTABLE PULSE GENERATOR HAVING A SINGLE PRINTED CIRCUIT BOARD AND A CHIP CARRIER

BACKGROUND OF THE INVENTION

This invention relates to improvements particularly applicable for use with implantable pulse generators such as cardiac pacers, nerve stimulators or fluid dispenser pumps and the like and will be described with particular reference thereto.

Although the invention will be described with particular reference to such implantable pulse generators, it is to be appreciated that the invention has applications with respect to improvements in electronic packaging suitable for other applications.

Implantable pulse generators such as cardiac pacers, nerve stimulators and fluid dispensing pumps are designed to be implanted within the human body for performing their intended function. Such generators typically include a hermetically sealed housing which contains a power supply in the form of a battery and a pulse generator circuit powered by the battery for providing pulses. The housing may, for example, be a metal case which is sealed so as to be effectively impervious with respect to either gases or liquids. Signals into and out of the circuitry are coupled through the casing by means of feedthrough terminals of various types known in the art. Examples of such a cardiac pacer may be found in the U.S. patent to A. Ushakoff U.S. Pat. No. 4,127,134, assigned to the same assignee as the present invention and in the U.S. patent to Greatbatch U.S. Pat. No. 4,135,519.

As is apparent from the above noted patents, the size of the housing is dependent upon that required to house both the battery and the electric circuit constituting the pulse generator. To a large extent, the size of the battery is dependent upon the anticipated lifetime as well as cost factors of the type of battery employed. In addition to improvements in batteries, great strides have been made in component packaging which greatly affects the size of the electric circuit employed. For example, the circuitry illustrated in the patent to Ushakoff, supra, shows discrete components as opposed to integrated circuits or chips as employed in the U.S. patent to A. F. Lesnick et al. U.S. Pat. No. 4,163,451, also assigned to the assignee herein. The Lesnick patent discloses a microprocessor based pulse generator for use as a cardiac pacer and includes integrated circuits including active chips such as microprocessors and other active circuits together with passive chips, such as chip resistors and chip capacitors. The use of such integrated circuits requires less space than discrete components and thus provides a reduction in the size necessary for the circuitry employed in such an implantable pulse generator.

It has been common in packaging such electronic circuitry to mount integrated circuits, or IC chips, as well as passive chips on a substrate or printed circuit board such that a considerable amount of the surface area was required to mount the various integrated circuits and other chips together with the interconnections from chip to chip. More recently, electronic packaging of such IC chips has included dual in-line (DIP) packaging.

Still further improvements in electronic packaging have included multi-layered ceramic carriers for housing and interconnecting one or more semiconductor integrated circuit chips such as that disclosed in the U.S. patent to Ibrahim et al. U.S. Pat. No. 4,320,438. This patent discloses a multi-layered ceramic package which is of square shape and is thin in terms of height. The upper surface has a cavity in which there is mounted a pair of IC chips with the cavity being hermetically sealed with a lid over the upper surface of the package. The IC chips have contact pads on their upper surfaces so that the chips may be interconnected to each other by way of wire bonds and wire bonding lands on one of the ceramic layers. Additionally, individual ones of the ceramic layers have metallized patterns thereon connected as by wire bonds to contact pads on the IC chips. Some of these metallized patterns extend to the peripheral edge of the package to contact edge metallizations or castellations. In some instances, the metallized patterns extend to a vertical conductive path or via which interconnects a metallized pattern on one ceramic layer with that on another ceramic layer, sometimes eventually leading to a peripheral edge metallization or castellation. The peripheral or edge castellations extend to the lowest surface of the package and connect with underlying contact pads. The underlying contact pads are located on the bottom surface adjacent the peripheral edge portion of the package. These contacts pads which serve as input-output (I/O) ports or terminals, may be connected to a mother board or a substrate on which the carrier is mounted.

In assembling the active chips and the passive chips of an implantable pulse generator such as the one disclosed in the patent to Lesnick, supra, the use of a chip carrier such as that disclosed in Ibrahim, supra, would permit the mounting of a pair of active chips in a hermetically sealed cavity of the chip carrier. While this might decrease the contact footprint required to mount the active chips, it may not improve the foot print area required for the additional components, such as chip resistors and chip capacitors which also must be interconnected with the active chips and other components to form the pulse generator.

SUMMARY OF THE INVENTION

The primary object of the present invention is to provide an improved implantable pulse generator having improvements in electronic packaging of the pulse generator circuitry so as to minimize the size of the casing to be implanted in the human body.

It is a still further object of the present invention to employ electronic packaging for the pulse generator including a chip carrier which in a single unit serves to mount and interconnect IC chips (active chips) and passive chips.

It is a still further object of the present invention to provide such a chip carrier wherein the integrated circuits are mounted in a hermetically sealed cavity located in one face of the chip carrier with the passive chips being mounted and electrically connected to bonding pads located on the opposite major surface of the chip carrier.

It is a still further object of the present invention to provide a chip carrier which is inverted such that the hermetically sealed cavity is on the bottom of the assembly together with suitable input/output contact pads for connection to a substrate to which the carrier is mounted. The passive chips are mounted and electrically connected to bonding pads located on the top surface of the carrier. The active chips are interconnected to the passive chips by means of metallized patterns located on various ceramic chip layers in a laminated construction together with vertically extending vias extending internally in a vertical direction through the ceramic layers to the bonding pads on the top surface.

In accordance with one aspect of the present invention, the pulse generator includes an implantable sealed housing of biocompatible material and which contains a power supply and a pulse generator circuit powered by the supply for providing pulses. The circuit includes a plurality of semiconductor chips including active chips and passive chips together with chip carrier means for carrying the semiconductor chips in a single structure. The active chips are mounted in a hermetically sealed cavity located in one of the major surfaces of the assembly and the passive chips are mounted to bonding pads located on the other major surface. The passive chips and active chips are electrically interconnected by way of a network of metallized paths located on the various ceramic layers together with vertically extending electrically conductive vias which extend through various of the layers to the passive chip mounting pads. Various of these metallized paths also extend laterally outward to metallized edges which extend along the peripheral edge of the assembly to I/O mounting pads on the bottom surface of the assembly so that the assembly may be electrically and physically mounted to a mother board or a substrate.

BRIEF DESCRIPTION OF THE DRAWINGS

The foregoing and other objects and advantages of the invention will become more readily apparent from the following description of the preferred embodiment of the invention as taken in conjunction with the accompanying drawings which are a part hereof and wherein.

DESCRIPTION OF THE PREFERRED EMBODIMENT

Figure 1:
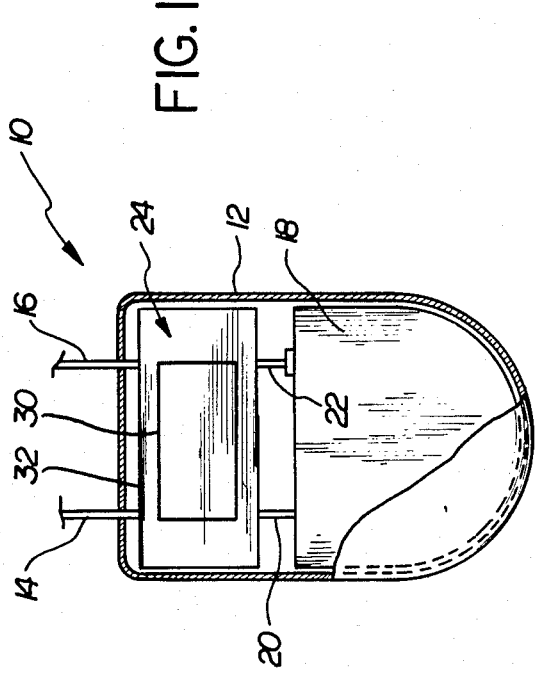
FIG. 1 is a plan view, with parts broken away, of a pulse generator constructed in accordance with the invention.

Reference is now made to the drawings and more particularly to FIG. 1 which illustrates an implantable pulse generator 10 and which takes the form of a cardiac pacer. The pulse generator includes a hermetically sealed housing 12, having a portion of its front face broken away to illustrate the contents therein. The casing 12 is preferably of a human compatible material such as stainless steel or titanium and it is designed to be implanted within the human body such that the contents within the casing are hermetically sealed while permitting a pair of electrodes 14 and 16 to extend therefrom. Additionally, the casing contains a battery 18 having cathode and anode terminals 20 and 22, respectively, connected to a pulse generator circuit generally designated at 24 so that power is supplied to the pulse generator circuit which in turns provides pulses to the electrodes 14 and 16 for stimulating a heart in a known manner. The pulse generator circuit 24 may take the form, for example, of that illustrated and described in U.S. patent to A. F. Lesnick et al. U.S. Pat. No. 4,163,451.

As presented in the Lesnick patent, supra, such a pulse generator circuit 24 includes a plurality of integrated circuits or active chips as well as a plurality of passive components such as chip capacitors and chip resistors. In accordance with the present invention, a plurality of these integrated circuits or active chips and a plurality of these passive chips are mounted on a chip carrier 30 which is, in turn, mounted on a mother board or a substrate 32. By so packaging these active and passive chips the physical size of the pulse generator circuit 24 is substantially reduced from that of prior art packaging techniques and, consequently, the size of the housing 12 is likewise reduced. The chip carrier and its construction are described in detail hereinafter with reference to FIGS. 2 through 9.

Figure 2:
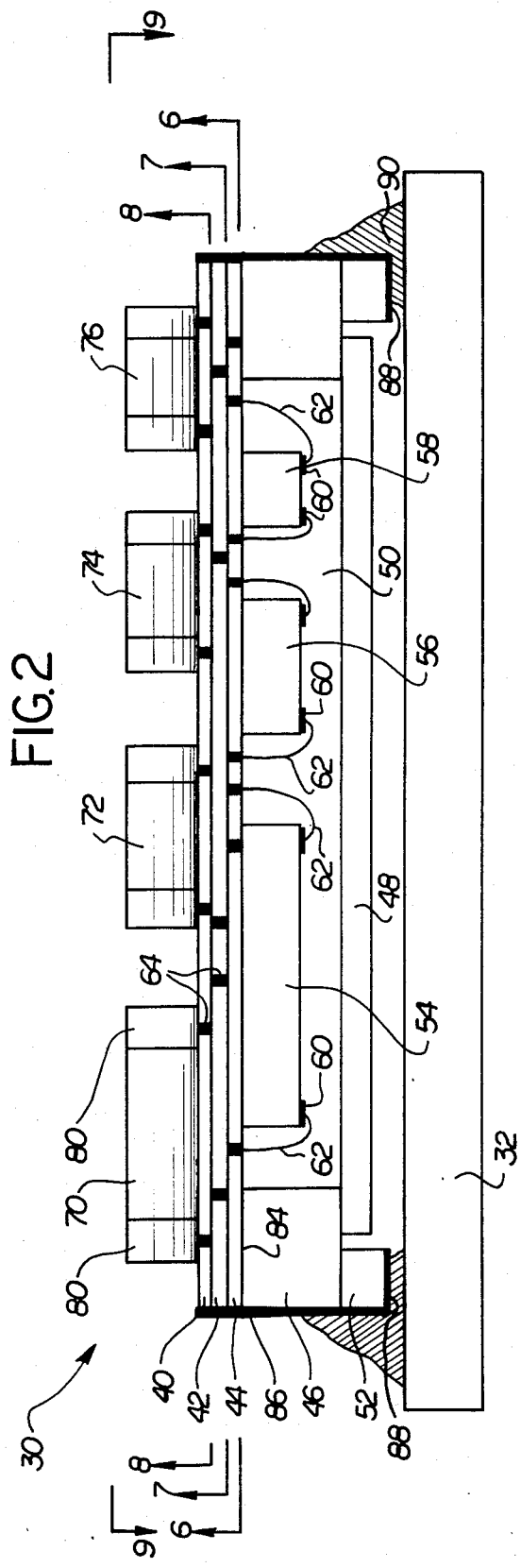
FIG. 2 is an elevational view schematically illustrating the pulse generator circuit on a substrate.

As seen in FIG. 2, the chip carrier 30 is a multi-layer ceramic package mounted on a mother board or a substrate 32. The chip carrier and the substrate are all constructed from ceramic material such as alumina ($Al_2O_3$). The chip carrier itself, in the embodiment of FIG. 2, employs several layers of ceramic material each having a pattern of conductive or metallized layers thereon. In the embodiment illustrated, this includes layers 40, 42 and 44. Additionally, the carrier includes an annular seal ring ceramic layer 46 to which a lid 48 is secured to form a hermetically sealed cavity 50, and lastly, an input/output annular layer 52 of a thickness greater than that of lid 48. Mounted within the cavity 50 to the bottom surface of ceramic layer 44 are integrated circuit chips 54 and 56 which may be termed as active chips together with another chip 58. Chip 58 may be an integrated circuit or active chip or may take the form, for example, of a thin film resistor or the like.

As is typical, the chips 54, 56 and 58 have an array of contact pads 60 on one major surface. These contact pads serve as input/output terminals for connecting the integrated circuits with other circuits, either passive or active, directly or by way of metallized layers on a mother board or in the case being described with metallized layers in a ceramic carrier. The other major surface of each chip 54, 56 or 58 is typically coated with a metallized layer such as a gold alloy and is frequently connected to ground by way of a circuit connection. As will be described in greater detail hereinafter, these chips are mounted on a metallized mounting pad on one of the ceramic layers and that mounting pad in turn connects the chip to circuit ground. The contact pads are connected to metallized patterns on the bottom surface of ceramic layer 44 by way of suitable wire bonds 62. These are typically gold wires approximately 0.001 inch in diameter (1 mil) and they interconnect associated contact pads on the chips with metallized patterns on ceramic layer 44.

The metallized patterns on layer 44 extend laterally of the chip on the bottom surface of layer 44 and in some instances terminate at an internal terminal which is then interconnected to patterns on other layers by way of vertical vias 64. These vertical vias are metallized vertically extending columns of conductive material which extend through the various ceramic layers 40, 42 and 44. They interconnect various of the metallized patterns vertically through the structure to mounting pads on the upper surface of ceramic layer 40. Various passive chips are mechanically and electrically connected to those mounting pads.

In the embodiment illustrated in FIG. 2, the passive chips include chips 70, 72, 74 and 76 all mounted on the upper surface of ceramic layer 40. These passive chips typically have metallized opposing ends 80 which serve as terminals for mechanical as well as electrical connection with the mounting pads on the upper surface of ceramic layer 40. A circuit path is thus completed by the vertical vias 64 to the appropriate contact pads 60 on the chips located in the hermetically sealed cavity 50.

Some of the horizontally extending conductive patterns on ceramic layers 40, 42, 44 and 46 extend laterally outward to the peripheral edges of the carrier. This is seen in FIG. 2 wherein a metallized layer 84 on the lower surface of ceramic layer 44 extends to the peripheral edge of the carrier where it connects with a vertically extending metallized groove or castellation 86. The castellations 86 extend vertically along the peripheral edges and connect with contact pads 88 located on the bottom surface of the input/output ring 52. It is to these I/O contact pads 88 that both mechanical and electrical connection is made to the mother board or substrate 32, such as by way of a lead-tin solder connection 90. Each solder connection electrically and mechanically interconnects a selected contact pad 88 with printed circuitry or the like located on the mother board 32.

Ceramic layers 40, 42, 44, and 46 and the input/output ring 52 may all be formed from green or uncured ceramic material, essentially of alumina ($Al_2O_3$). This material is typically furnished in sheets and are shaped by pressing, molding and punching to conform to the configurations as seen in the drawings herein. The metallized layers or conductive patterns, such as layer 84 on the bottom surface of ceramic layer 44 may typically be produced by deposition procedures using masking or screening techniques to apply successive layers of suitable metals such as a layer of tungsten applied directly to the ceramic material. These are covered with a layer of nickel and finally a layer of gold both of which are plated layers. The vertical vias 64 in FIG. 2 are formed by making vertical holes through the ceramic layers where they interconnect with internal terminals at the internal ends of metallized layers. The holes are then filled with a metallic paste which converts to a solid electrically conductive form. Where lid 48 makes contact with seal ring 46, the bonding between the two layers may be obtained from a gold-tin preform which when heated, on the order of 300° C., forms a hermetic seal so that the active chips and their wire bondings are located in a protected environment within the cavity 50.

Figure 3:
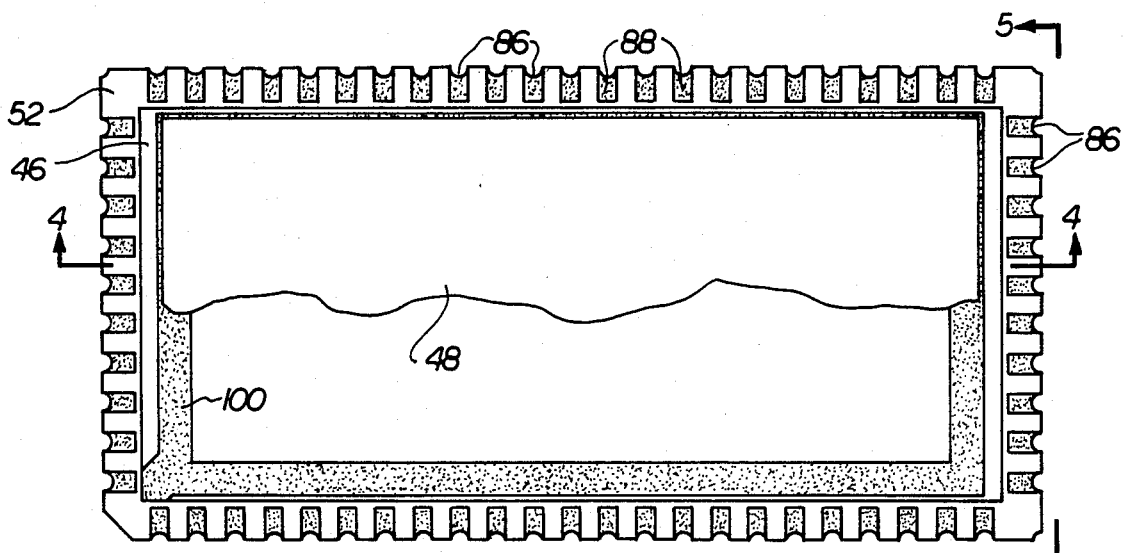
FIG. 3 is a plan view, with parts broken away, of the chip carrier.
Figure 4:
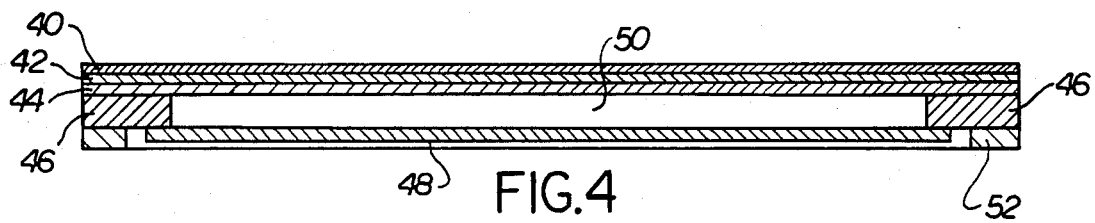
FIG. 4 is a sectional view taken generally along line 4—4 looking in the direction of the arrows in FIG. 3.
Figure 5:
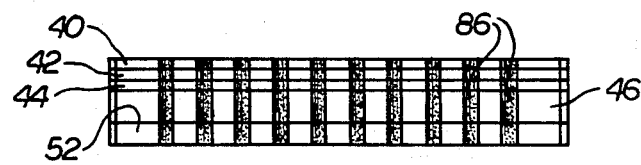
FIG. 5 is an end view taken generally along line 5—5 looking in the direction of the arrows in FIG. 3.

Attention is now directed to FIGS. 3, 4 and 5 which illustrate the composite chip carrier, but without the active and passive chips being mounted thereto. FIG. 3 is a view looking upward at the bottom of the chip carrier with a portion of lid 48 being broken away to reveal a metallized pattern 100 on seal ring 46. The input/output ring 52 is shown in FIG. 3 which reveals the pattern of the input/output contact pads 88 located on the bottom surface of the chip carrier. The input/output contact pads 88 are in electrical communication with the metallized edge castellations 86 along the peripheral edge of the carrier, as is best seen in FIGS. 3 and 5.

Figure 6:
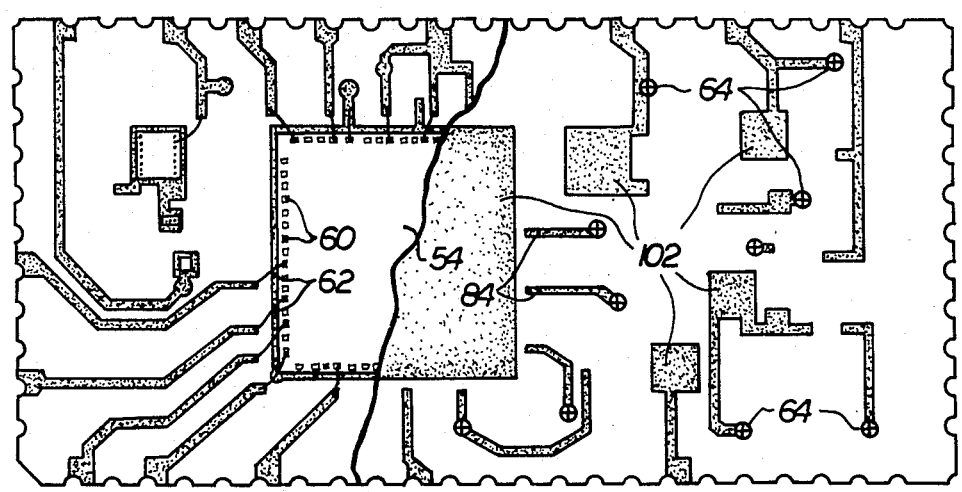
FIG. 6 is a view taken generally along line 6—6 looking in the direction of arrows in FIG. 2.

Reference is now made to FIG. 6 which illustrates the bottom surface of the ceramic layer 44 with the metallized patterns thereon together with a showing of some of the integrated circuits and their mounting. Layer 44 is a solid layer rather than being annular and includes enlarged metallized layer sections that serve as integrated circuit mounting pads such as mounting pads 102 to which integrated circuits may be mounted. The smaller mounting pads may mount transistors or passive components. Some of the metallized conductive patterns which extend laterally along the surface of layer 44 extend from the mounting pads and terminate at internal terminals connecting to vertical vias 64. Some of the conductive patterns 84 extend to the peripheral edge castellations 86 with the conductive patterns 84 being connected by wire bonding 62 to various input/output contact pads 60 on the integrated circuit chips, such as chip 54.

Figure 7:
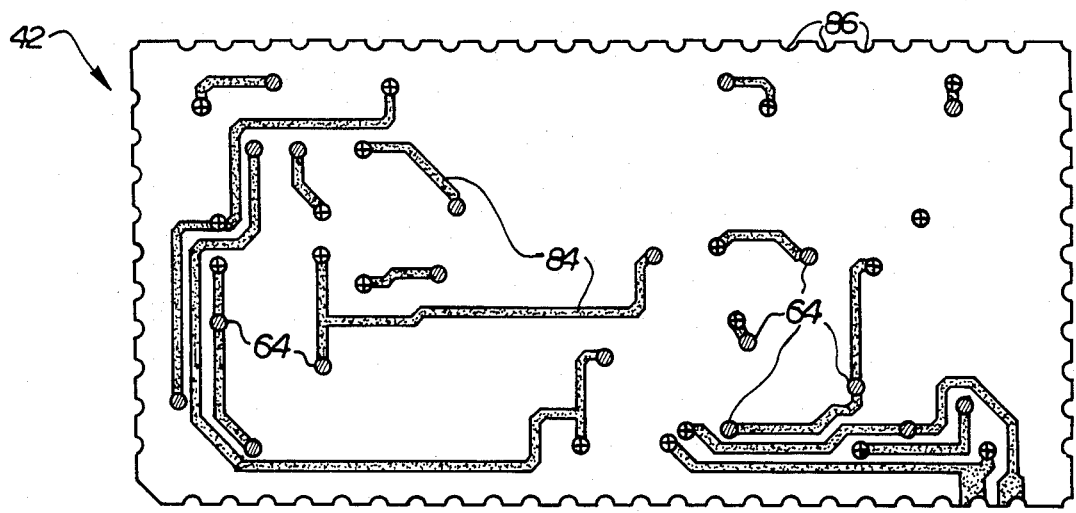
FIG. 7 is a view taken generally along line 7—7 looking in the direction of the arrows in FIG. 2.

FIG. 7, in a manner similar to that of FIG. 6, illustrates the metallized patterns on the bottom surface of ceramic layer 42. Here there is shown lateral conductive patterns 84 which connect internally with vias 64 so as to make vertical connection from layer to layer and/or with the external or peripheral castellations 86 so as to make electrical connection with the input/output contact pads 88 on the bottom of the chip carrier. Additionally, some of the conductive patterns 84 make contact with a land area for a via 64 extending vertically from layer 44. Additionally, some of the conductive patterns make contact with vias 64 which commence at that level and go to the next level. This is shown by the code of land areas and vias shown in connection with FIG. 7 herein.

Figure 8:
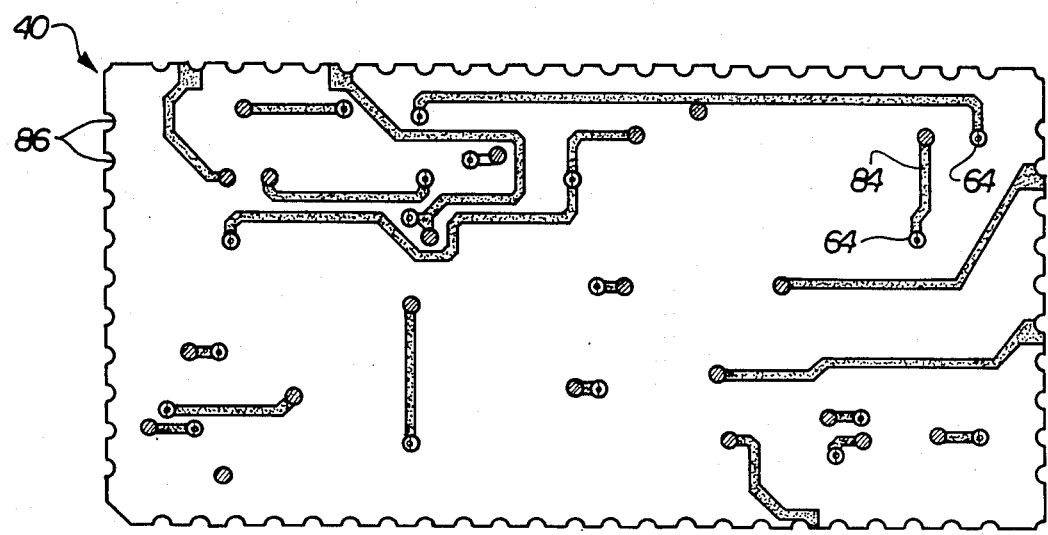
FIG. 8 is a view taken generally along line 8—8 looking in the direction of the arrows in FIG. 2.

FIG. 8 is similar to FIG. 7 but shows the metallized patterns on the bottom surface of ceramic layer 40, as viewed in FIG. 2. As in the case of FIG. 7, FIG. 8 illustrates laterally extending conductive patterns 84 some of which extend to edge castellations 86, others of which make connection with internal vias 64. The landing areas for the vias on the bottom surface of ceramic layer 40 are indicated by the code shown in FIG. 8.

Figure 9:
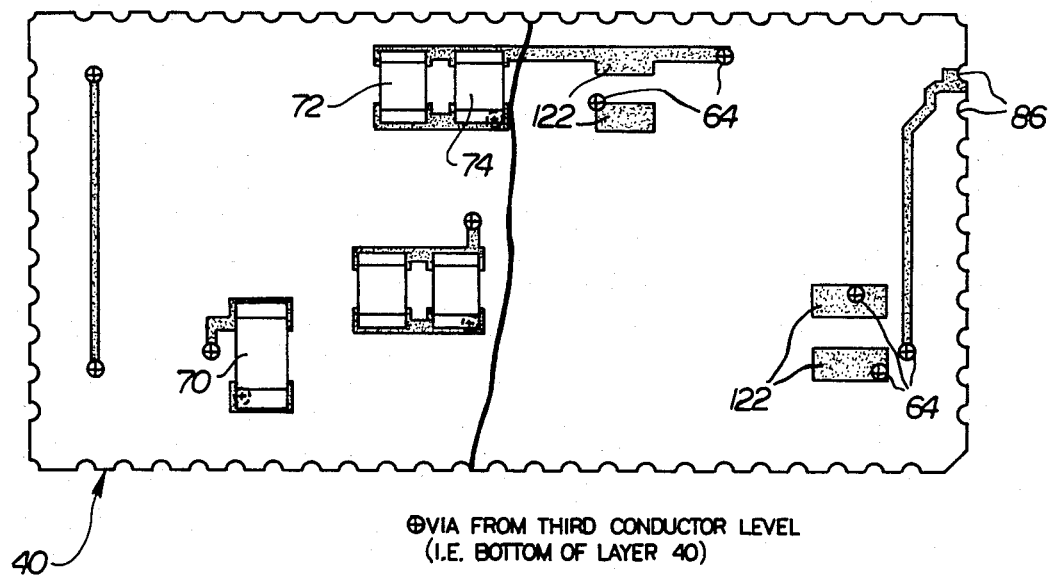
FIG. 9 is a view taken generally along line 9—9 looking in the direction of the arrows in FIG. 2.

Reference is now made to FIG. 9 which illustrates on the right side of the Figure the metallization patterns without the components being mounted thereon and on the left side the metallization patterns with various passive chips being mounted thereto. Various of the vias 64 extend to the top surface of layer 40 and terminate in enlarged metallized areas or contact pads 122 to which the end terminals 80 of a passive chip may be mechanically and electrically secured, as with a suitable solder or conductive epoxy or the like. Some of the vias 64 as they terminate on the upper surface of layer 40 may connect to conductive patterns which extend laterally to make contact with selected edge castellations 86. As is seen in the left side of FIG. 9, passive chip components such as a thick film resistor 72 and a thick film capacitor 74 are mounted on the upper surface of layer 40 to the mounting pads 122.

Although the invention has been described in conjunction with a preferred embodiment, it is to be appreciated that various modifications and arrangements may be made without departing from the spirit and scope of the invention as defined by the appended claims.

What is claimed is:

1. An implantable pulse generator comprising:

a human implantable sealed housing of biocompatible material and containing a power supply and a pulse generator circuit powered by said supply for supplying pulses, said circuit including a plurality of semiconductor chips including active chips and passive chips, a single printed circuit mother board for carrying said chips, and chip carrier means mounted on said mother board and carrying said semiconductor chips wherein said carrier means includes:

a unitized body comprised of a plurality of ceramic layers fused together, said body having oppositely facing major surfaces, a cavity disposed in only a first of said major surface housing a plurality of said active chips and a lid member covering and sealing said cavity, the second of said major surfaces having a plurality of conductive mounting pads thereon electrically receiving and mounting said passive chips thereto whereby said passive chips are mounted on one of said major surfaces and said active chips are mounted and carried in said cavity in the other of said major surfaces.

2. An implantable pulse generator as set forth in claim 1, wherein said cavity has a floor on one of said ceramic layers with said floor having metallized patterns thereon including metallized mounting pads electrically and mechanically mounting said active chips.

3. An implantable pulse generator as set forth in claim 2 including a pattern of metallized vertical vias extending through various of said ceramic layers.

4. An implantable pulse generator as set forth in claim 3 wherein each said layer has a network of laterally extending metallized patterns thereon, some of said patterns making electrical contact with a said via to thereby electrically interconnect patterns on different layers.

5. An implantable pulse generator as set forth in claim 4 wherein some of said vias extend to said floor surface and connect with some of said metallized patterns thereon.

6. An implantable pulse generator as set forth in claim 5 wherein said active chips have an array of input/output contact pads thereon, and wire bonding connecting some of said input/output pads with some of said metallized patterns on said floor surface, whereby some of said input/output contact pads on said active chips may be interconnected by said metallized patterns on said layers and by said vias with the passive chips mounted to said contact pads on said second major surface.

7. An implantable pulse generator as set forth in claim 5 including a pattern of spaced apart metallized castellations on the peripheral edges of said carrier, said castellations extending vertically between said first and second major surfaces, some of said metallized patterns on said layers extending laterally to and connecting with some of said edge castellation so as to make electrical contact therewith.

8. An implantable pulse generator as set forth in claim 5 including a plurality of input/output contact pads located on the bottom surface of said carrier with each input/output contact pad being in electrical connection with one of said edge castellations.

9. An implantable pulse generator as set forth in claim 3 wherein some of said vias extend vertically to said second major surface and electrically connect with said mounting pads thereon so as to thereby electrically connect said passive chips with some of said metallized patterns.

* * * * *